(12) United States Patent
Yoshiba

(10) Patent No.: US 9,114,044 B2
(45) Date of Patent: Aug. 25, 2015

(54) ABSORBENT ARTICLE

(71) Applicant: DAIO PAPER CORPORATION, Shikokuchuo-shi, Ehime (JP)

(72) Inventor: Megumi Yoshiba, Sakura (JP)

(73) Assignee: DAIO PAPER CORPORATION, Ehime (JP)

( * ) Notice: Subject to any disclaimer, the term of this patent is extended or adjusted under 35 U.S.C. 154(b) by 0 days.

(21) Appl. No.: 14/348,695

(22) PCT Filed: Sep. 28, 2012

(86) PCT No.: PCT/JP2012/075011
§ 371 (c)(1),
(2) Date: Mar. 31, 2014

(87) PCT Pub. No.: WO2013/047716
PCT Pub. Date: Apr. 4, 2013

(65) Prior Publication Data
US 2014/0243773 A1    Aug. 28, 2014

(30) Foreign Application Priority Data

Sep. 30, 2011 (JP) ................................. 2011-216518

(51) Int. Cl.
*A61F 13/58* (2006.01)
*A61F 13/56* (2006.01)
*A61F 13/472* (2006.01)
*A61F 13/47* (2006.01)
*A61F 13/476* (2006.01)

(52) U.S. Cl.
CPC ............ *A61F 13/5616* (2013.01); *A61F 13/472* (2013.01); *A61F 13/4704* (2013.01); *A61F 13/476* (2013.01); *A61F 13/47245* (2013.01)

(58) Field of Classification Search
CPC ............ A61F 13/47245; A61F 13/476; A61F 13/5616
See application file for complete search history.

(56) References Cited

U.S. PATENT DOCUMENTS

| 2004/0133179 | A1* | 7/2004 | Steger et al. ............. 604/385.04 |
| 2004/0267224 | A1* | 12/2004 | Ulman ..................... 604/385.04 |
| 2005/0124959 | A1* | 6/2005 | Alcantara et al. ........ 604/385.04 |
| 2005/0131372 | A1* | 6/2005 | Wheeler et al. .......... 604/385.04 |
| 2006/0149202 | A1* | 7/2006 | Cardin et al. ............. 604/385.04 |
| 2009/0204095 | A1* | 8/2009 | McDaniel ..................... 604/387 |
| 2010/0305539 | A1* | 12/2010 | Odoi ........................ 604/385.01 |
| 2010/0312215 | A1  | 12/2010 | Odoi |
| 2011/0004179 | A1* | 1/2011 | Kurihara .................. 604/385.02 |

(Continued)

FOREIGN PATENT DOCUMENTS

| JP | 2004-290602 | 10/2004 |
| JP | 2009-125430 | 6/2009 |

(Continued)

*Primary Examiner* — Susan Su
(74) *Attorney, Agent, or Firm* — Jordan and Hamburg LLP

(57) ABSTRACT

An absorbent article such as a sanitary napkin has a respective wing-shaped flap extending outward from each side of the main body of the absorbent article. Each wing-shaped flap has a front profile line and a rear profile line. The front profile line is a wave-shape formed by a repetition of convex portions and concave portions. The angle between a line connecting the vertex of the outermost concave portion of the wing-shaped flap with the origin point of the front profile line of the wing-shaped flap and another line originating at the origin point of the front profile line of the wing-shaped flap is 60-65°.

5 Claims, 10 Drawing Sheets

(56) References Cited

U.S. PATENT DOCUMENTS

2013/0116646 A1* 5/2013 Robles .................. 604/369
2013/0123731 A1* 5/2013 Mercer et al. ............ 604/385.04
2013/0310791 A1* 11/2013 Malowaniec ............ 604/385.04

FOREIGN PATENT DOCUMENTS

| | | |
|---|---|---|
| JP | 2009-131442 | 6/2009 |
| JP | 4641979 | 12/2010 |

* cited by examiner

RELATED ART

RELATED ART

ABSORBENT ARTICLE

BACKGROUND OF THE INVENTION

The present invention relates to an absorbent article provided with wing-shaped flaps which are wrapped around the crotch section of underwear upon securing the absorbent article onto the underwear.

Conventionally, as absorbent article (N) such as sanitary napkins, panty liners, vaginal secretion-absorbing sheets, and urinary incontinence pads, etc., for example as illustrated in FIG. 10, a configuration in which absorbent body (52) consisting of a cotton-like pulp, etc. interposed between liquid-impermeable backing sheet (50) consisting of polyethylene sheets or polyethylene-laminated non-woven fabrics, etc., and liquid-permeable surface sheet (51) consisting of non-woven fabrics or porous plastic sheets has been known.

As such type of absorbent article (N), in order to prevent displacement while in the state of being attached, for example there exists a configuration in which one or a plurality of strips of adhesive layer (53, 53) are formed on the non-skin contacting surface (outer surface), wing-shaped flaps (W, W) which extend outwards are integrally formed on both sides of the napkin main body in relation to the longitudinal direction thereof, and adhesive layers (54, 54) are provided on the surface of liquid-impermeable backing sheet (50) (outer surface) of these wing-shaped flaps (W, W).

In order to secure the absorbent article (N) onto underwear (60), as illustrated in FIG. 11, the underwear is worn on the body after absorbent article (N) is positioned on underwear (60) at a position corresponding to the crotch, the wing-shaped flaps (W, W) which protrude to the side are made to protrude further outwards than the underwear, and both wing-shaped flaps (W, W) are folded back at fold lines (RL, RL) to adhere to the outer surface of the crotch area of underwear (60) while wrapping around the crotch section of the underwear.

However, when folding back the wing-shaped flaps, if these were folded back carelessly, such could cause incorrect adhesion where only a single part is folded back and the adhesives adhere to each other to create wrinkles or a ridged area or where a wing-shaped flap is folded back halfway and the adhesives adhere to each other. In addition, in cases when the flaps are not being properly folded back at fold line (RL), the fold lines of the wing-shaped flaps are folded back in a diagonally bent manner, and this protruding section created where the flaps are folded back would cause problems such as discomfort around the legs and displacement of the absorbent article which may even lead to leaks, etc.

Therefore, a variety of means to increase the fixity of the wing-shaped flaps in relation to the underwear (hereinafter, also referred to as panties) have been proposed. For example, disclosed in Japanese Patent Publication No. 4641979 is an absorbent article having an absorbent main body, having an absorbing layer and a leakage preventing layer, and a pair of wing sections which are provided on both sides of the absorbent main body along the portion facing excretory area and are secured onto underwear by being folded hack towards the non-skin facing surface of the underwear, wherein the shape of each wing section of the pair is asymmetrical in relation to a lateral transverse line passing through the midpoint of the edge of the distal end on each wing section, each wing section of the pair is configured such that the rear to front angle of inclination of the rear edge of the wing in relation to the longitudinal axis of the absorbent main body is smaller than the rear to front angle of inclination of the front edge of the wing in relation to the longitudinal axis of the absorbent main body, the front edge of each wing of the pair is straight, and the rear edge of each wing of the pair is of a continuous wave shape.

In addition, disclosed in Japanese Unexamined Patent Publication No. 2009-125430 is an absorbent article with wing-shaped flaps which are formed on both sides of the section of the main body where an absorbent body is interposed between a liquid-permeable surface sheet and a liquid-impermeable backing sheet and are each secured by wrapping around the crotch section of underwear when being attached, wherein the wing-shaped flaps have a front edge profile line that extends outwards from the main body section and a rear edge profile line that extends outwards from the main body section, the angle formed by a line along the lateral direction of the absorbent article and the rear edge profile line is greater than the angle formed by a line along the lateral direction of the absorbent article and the front edge profile line, and the center of gravity of the wing-shaped flaps is offset to be on the front side of the center of the line where the base of each wing-shaped flap is connected to the main body section. Furthermore, it is also disclosed in this Japanese Unexamined Patent Publication No. 2009-125430 that the front edge profile line and rear edge profile line are wave-shaped, curved, or a combination of being both wave-shaped and curved.

SUMMARY OF THE INVENTION

Although the absorbent articles described in Japanese Patent Publication No. 4641979 and Japanese Unexamined Patent Publication No. 2009-125430 are configured to enable the wing-shaped traps to be properly folded back along the side edges of the crotch of panties and can be expected to be significantly effective in comparison to conventional trapezoidal wing-shaped flaps, when a hand is placed along a wing-shaped flap to fold the flap back, although fingers conic in contact with the front edge profile line of the wing-shaped flap, when the front edge profile line is of a straight shape as in the napkin according to the abovementioned Japanese Patent Publication No. 4641979, failures would occur in folding the flap hack due to there not being a section for the fingers to catch onto. Furthermore, although the abovementioned Japanese Unexamined Patent Publication No. 2009-125430 discloses a configuration in which the front edge profile line is wave-shaped, curved, or a combination of being both wave-shaped and curved, if the fingers are not positioned in an appropriate position of the wing-shaped flaps, failures would still occur in folding the flaps back and prevent the flaps from being folded back properly along the side edges of the panties.

Thus, the main problem addressed by the present invention is to provide an absorbent article that enables wing-shaped flaps to be properly folded back at their correct folding positions (base positions) along the side edges of panties.

As first aspects of the present invention, provided in order to resolve the abovementioned problem is: an absorbent article with wing-shaped flaps which are formed on both sides of the section of the main body where an absorbent body is interposed between a liquid-permeable surface sheet and a liquid-impermeable hacking sheet and are each secured by wrapping around the crotch section of underwear when being attached, wherein the wing-shaped flaps have a front edge profile line that extends outwards from the main body section and a rear edge profile line that extends outwards from the main body section, wherein the front edge profile line is a wave-shaped line formed by a repetition of convex portions that protrude outwards and concave portions that protrude inwards and a straight line, connecting the vertex of the concave portion positioned in the most outwards position and the connecting point where the rear edge profile line of the wing-shaped flaps connects to the main body section of the absorbent article, is configured to be at an angle of 60-65° in relation to a line orthogonal to a longitudinal direction or axis of the absorbent article, passing through the connecting point.

The concave portion positioned in the most outwards position is configured as the position where the index finger of a hand catches on. In light of the results of the present inventors having studied the direction and position in which hands are placed upon the user folding back the wing-shaped flaps, it was discovered that the index finger was most likely to be positioned in a direction where a straight line, connecting the vertex of the concave portion positioned in the most outwards position and the connecting point where the rear edge profile line of the wing shaped flaps connects to the main body section of the absorbent article, is at an angle of 60-65° as described above, the position of the concave portion was configured in the abovementioned manner, enabling the wing-shaped flaps to be properly folded back at their correct folding positions (base positions) along the side edges of panties by improving the ease of folding back the wing-shaped flaps with a configuration that enables the index finger to catch on to the concave portion when the user folds the wing-shaped flaps back.

The aforementioned 60-65° angle may be referred to as angle α.

According to another aspect of the present invention to, the angle β formed by a line originating at the connection point of the rear profile line and extending orthogonally of a lengthwise direction or axis of the absorbent article and a line originating at the absorbent article and the rear edge profile line is configured to be greater than the angle θ formed by the front edge profile line and a line originating at the connection point of the front profile line and extending orthogonally of a lengthwise direction or axis of the absorbent article, and the center of gravity of each of the wing-shaped flaps is offset to be forward of the center of the line extending between the front and rear connection points.

In other words, a non-isosceles trapezoid shape or approximate triangle shape, wherein the slant of the edge on the rear side of the flap is steeper than that of the edge on the front side, is adopted in place of the conventional flap shape of an isosceles trapezoid. By having such outer shape, as will be described in greater detail below, it becomes easier for the flaps to be properly and easily folded back at their correct folding positions. Furthermore, the straight line used to determine angle (θ) formed by the front edge profile line is the directional line of the wave-shaped line that comes into contact with the convex portion positioned in the most outwards position. In addition, the straight line used to determine angle (β) formed by the rear edge profile line, in the case that the rear edge profile line is a wave-shaped line, similar to with the front edge profile line, is the directional line of the wave-shaped line that comes into contact with the convex portion positioned in the most outwards position.

By having the abovementioned outer shape, as will be described in greater detail below, it becomes possible for the wing-shaped flaps to be properly and easily folded back at their correct folding positions and adhered without causing problems such as adhesives adhering to each other and incorrect adhesion, etc.

The radius of curvature of the concave portion is, preferably, configured to be greater than or equal to 10 mm yet less than or equal to 20 mm in order to make it easier for the index finger of a hand to catch onto the concave portion.

The distance between the aforementioned front and rear connecting points is, preferably, less than or equal to 80 mm and the protruding length, i.e., the distance from base to tip measured orthogonally to a lengthwise direction or axis of the absorbent article, of the wing-shaped flaps is greater than or equal to 40 mm. Namely, the wing-shaped flaps are configured to be less than or equal to 80 mm to fit within the curved portion of the crotch of panties and the protruding length of the wing-shaped flaps is configured to be greater than or equal to 40 mm to make it easier for these flaps to be pressed on by a hand when being folded back. A cutout portion that dips into the main body section of the absorbent article may be provided in the area of the front and rear connection points to facilitate the wing-shaped flaps being easily folded hack at their origin.

As explained in detail in the above, the above configuration enables the wing-shaped flaps to be properly folded back at their correct folding positions (base positions) along the side edges of panties.

BRIEF DESCRIPTION OF THE DRAWINGS

FIG. 5A is in the case of a conventional wing-shaped flap and 5B is in the case of a wing-shaped flap according to the present invention.

FIG. 6A is in the case of a conventional wing-shaped flap and FIG. 6B is in the case of a wing-shaped flap according to the present invention.

DETAILED DESCRIPTION OF THE INVENTION

Figure 1:
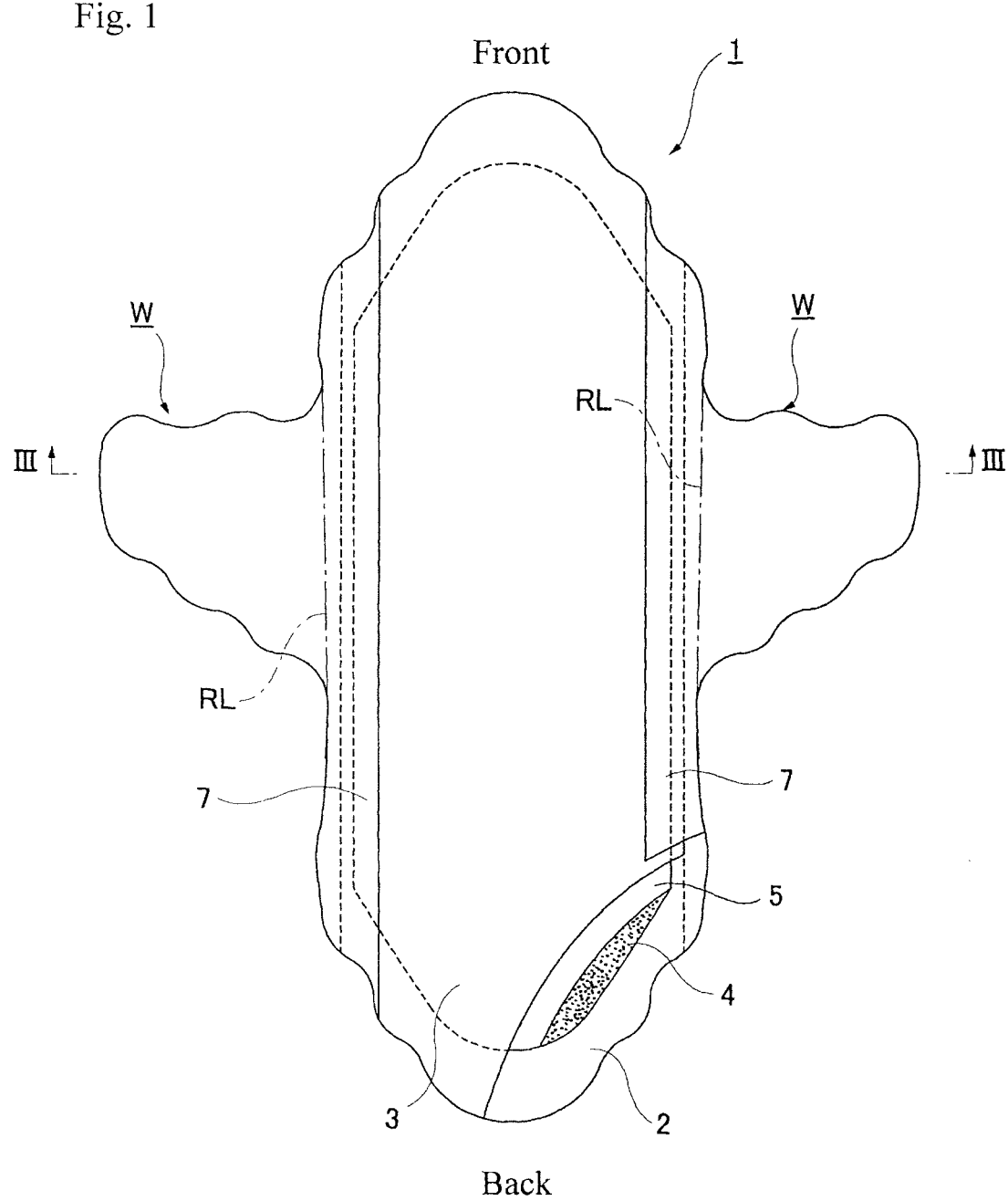
FIG. 1 is a partially ruptured development view of sanitary napkin (1) according to the present invention.

Embodiments of the present invention are explained below in detail with reference to the drawings.

Sanitary napkin (1) according to the present invention is configured of: liquid-impermeable backing sheet (2) consisting of a polyethylene sheet or polypropylene sheet, etc., liquid-permeable surface sheet (3) that allows menstrual blood and vaginal secretions to quickly permeate, absorbent body (4) that consists of a cotton-like pulp or a synthetic pulp, etc. and is interposed between the two sheets (2, 3), creped paper (5) that encloses the absorbent body (4) for the purpose of retaining the shape and improving the diffusibility of absorbent body (4), second sheet (6) that consists of a hydrophilic non-woven fabric and is interposed between the liquid-impermeable surface sheet (3) and creped paper (5), and side non-woven fabric (7, 7) formed respectively along the longitudinal direction on both side sections of the surface. In the surrounding of the absorbent body (4), at the top and bottom end edge sections, the outer edge sections of the liquid-impermeable backing sheet (2) and liquid-permeable surface sheet (3) are joined by an adhesive such as hot-melt, etc. or an adhesive means such as heat-sealing, etc. and at both side edge sections thereof, the side non-woven fabric (7) and the liquid-impermeable backing sheet (2) extending further to the side than absorbent body (4) are joined by an adhesive such as hot-melt, etc. or an adhesive means such as heat-sealing, etc.

To further explain the structure of the sanitary napkin (1) below in detail:

for the liquid-impermeable backing sheet (2), although a sheet material having at least impermeability such as an olefin-based resin sheet, etc. of polyethylene or polypropylene, etc. is used, apart from such, it is also possible to use a laminated non-woven fabric consisting of a non-woven fabric laminated onto a polyethylene sheet, etc. or even a non-woven sheet upon essentially ensuring impermeability by interposing a waterproof film (in such case the liquid-impermeable backing sheet is to be configured of a waterproof film and a non-woven fabric). In recent years, there is a tendency where a material having permeability is used from the perspective of preventing moisture from building up. This impervious yet moisture permeable sheet material is a microporous sheet obtained by melt kneading inorganic filler into an olefin-based resin such as polyethylene or polypropylene, etc. to form a sheet and subsequently extending this uniaxially or biaxially.

For the liquid-permeable surface sheet (3), a porous or nonporous non-woven fabric or a porous plastic sheet, etc. can be suitably used. The fiber material configuring the non-woven fabric, may be for example, apart from synthetic fibers that are olefin-based such as polyethylene or polypropylene, polyester-based, or polyamide-based, etc., recycled fibers such as cupro or rayon, etc. or natural fibers such as cotton, etc. and it is possible to use a non-woven fabric obtained by a suitable processing method such as the spun lacing method, the spun bonding method, the thermal bonding method, the melt blown method, and the needle punching method, etc. Of these processing methods, the spun lacing method is superior in terms of flexibility and draping ability of fabric thereby produced while the thermal bonding method is superior in terms of bulk and softness of fabric, thereby produced. Furthermore, it is desirable to apply embossing in any of various shapes on the top surface of the liquid-permeable surface sheet (3) in order to prevent leakage from the sides by promoting the retention of bodily fluids and increasing the efficiency of absorption.

Absorbent body (4) interposed between the liquid-impermeable backing sheet (2) and liquid-permeable surface sheet (3) is for example configured of a fluffed pulp and a water-absorbing polymer. The water-absorbing polymer is for example mixed into the pulp configuring the absorbent body as a granular powder. As the pulp, those consisting of cellulose fibers of a chemical pulp obtained from wood or a dissolving pulp, etc. and artificial cellulosic fibers such as rayon or acetate can be listed, and a softwood pulp of a long fiber length is preferably used over a hardwood pulp in terms of its function and price. As in this example, in eases when creped paper (5) that encloses absorbent body (4) is provided, creped paper (5) ends up being interposed between liquid-permeable surface sheet (3) and absorbent body (4), and due to the creped paper (5) having excellent absorbency, bodily fluids are quickly diffused and such menstrual blood, etc. is prevented from flowing in the reverse direction.

Second sheet (6) that consists of a hydrophilic non-woven fabric and is interposed between the liquid-permeable surface sheet (3) and creped paper (5) may be for example, apart from synthetic fibers that are olefin-based such as polyethylene or polypropylene, polyester-based, or polyamine-basest, etc., recycled fibers such as cupro or rayon, etc. or natural fibers such as cotton, etc. and it is possible to use a non-woven fabric obtained by a suitable processing method such as the spun lacing method, the spun bonding method, the thermal bonding method, the melt blown method, and the needle punching method, etc. In order to realize the hydrophilic property, it is possible to make a synthetic fiber swollen or porous by such as a method in which a compound having a hydrophilic group, for example an oxidized product of polyethylene glycol, etc., is allowed to coexist and be polymerized in the manufacturing process of the synthetic fiber or a method in which treatment is performed with a metallic salt such as stannic chloride to partially dissolve the surface to create a porous surface and a hydroxide of a metal is deposited in order to realize the hydrophilic property as an application of the capillary phenomenon. Furthermore, the abovementioned second sheet (6) is preferably used in a combination where liquid-permeable surface sheet (3) is a porous plastic sheet.

Meanwhile, at both sides of the present sanitary napkin (1), side non-woven fabric (7, 7) is provided respectively along the longitudinal direction and almost throughout the entire length of napkin (1), and a part of this side non-woven fabric (7, 7) extends sideways, together with a part of liquid-impermeable hacking sheet (2) similarly extending sideways, to form wing-shaped flaps (W, W). This wing-shaped flap (W) will be later described in detail.

As the side non-woven fabric, it is possible to use a non-woven fabric treated to be water-repellant or a non-woven fabric treated to be hydrophilic depending on which functions are considered more important. For example, if an importance is being placed on a function such as preventing menstrual blood or vaginal secretions, etc. from permeating or improving the touch, etc. it is preferable to use a non-woven fabric that is treated to be water-repellant by being coated with a silicone-based, paraffin-based, or alkyl-chromic chloride-based water-repellent. In addition, if an importance is being placed on the absorbency of menstrual blood, etc. in the wing-shaped flaps (W, W), it is suitable to use a non-woven fabric treated to be hydrophilic with a synthetic fiber made to be swollen or porous by such as by a method in which a compound having a hydrophilic group, for example an oxidized product of polyethylene glycol, etc., is allowed to coexist and he polymerized in the manufacturing process of the synthetic fiber or a method in which treatment is performed with a metallic salt such as stannic chloride to partially dissolve the surface to create a porous surface and a hydroxide of a metal is deposited in order to realize the hydrophilic property as an application of the capillary phenomenon.

Figure 2:
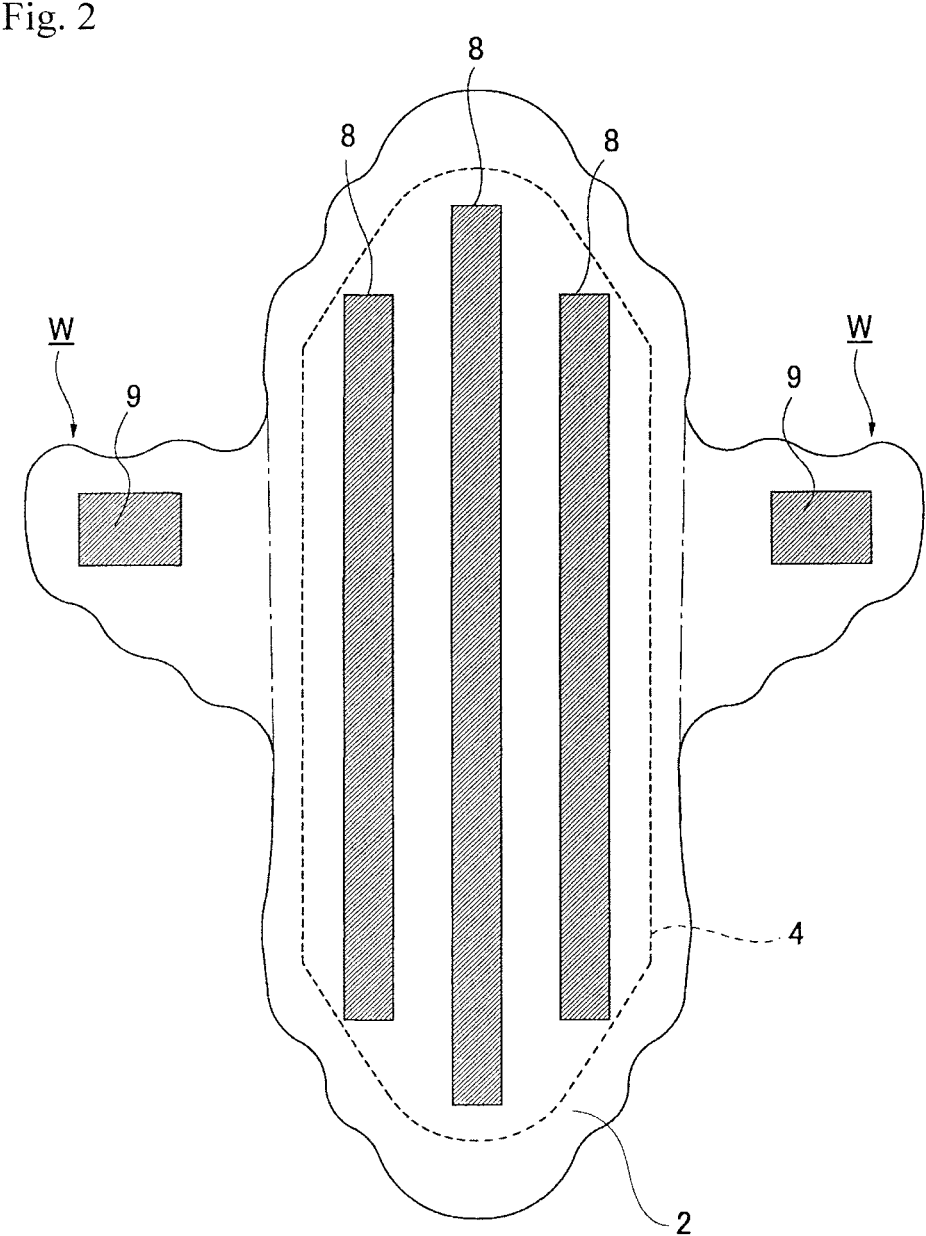
FIG. 2 is a rear surface view of the same.
Figure 3:
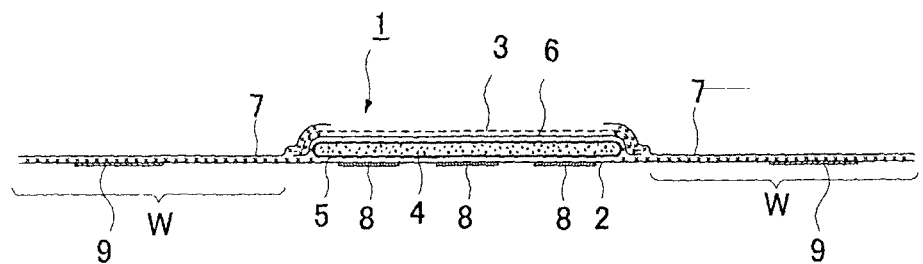
FIG. 3 is a diagram viewed from the arrows along line III-III of FIG. 1.

As illustrated in FIG. 2, while on the non-skin contacting surface of the main body section where absorbent body (4) is interposed between the liquid-permeable surface sheet (3) and liquid-impermeable backing sheet (2), a plurality of strips, or in the illustrated example three strips, of a main body displacement preventing adhesive layer (8, 8 . . . ) are formed according to an appropriate application pattern for the purpose of being fixed onto the underwear, these main body displacement preventing adhesive layers (8, 8 . . . ) are covered with a separating material (not shown) covering the main body. In addition, wing displacement preventing adhesive layers (9) are formed on the surface of liquid-impermeable backing sheet (2) of the wing-shaped flaps (W, W) and these wing displacement preventing adhesive layers (9, 9) are covered with a separating material (not shown) for the wings. The separating materials are preferably configured such that the separating material for the main body and the separating material for the wings arranged in a transverse direction are joined at an intersecting section to enable the separating materials to be removed in a single peeling step and the wing-shaped flaps (W, W), when individually packaged, may be folded towards the liquid-permeable surface sheet (3), or in other words folded forwards, or folded towards of liquid-impermeable backing sheet (2), or in other words folded backwards. In addition, the separating material covering wing displacement preventing adhesive layers (9, 9) may be a separate, individual sheet for each wing instead of being a single sheet for both wings.

As the separating material, it is possible to use a plastic sheet or paper treated to be separable by means of a release treatment solution such as a silicone-based resin, fluorine-based resin, or a tetafluoroethylene-based resin, etc. painted or spray coated onto the surface to be placed in contact with displacement preventing adhesive layers (8, 9).

As the adhesive forming the displacement preventing adhesive layers (8, 9) it is suitable to use, for example, an adhesive in which the main component is any one of a styrene-based polymer, a tackifier, or a plasticizer. As the styrene-based polymer, although styrene-ethylene-butylene block copolymers, styrene-butylene-styrene block copolymers, styrene-isobutylene-styrene copolymers, and styrene-butadiene-styrene block copolymers, etc. can be listed, a single selection from these may be used or the polymer may also be a polymer blend of two or more types. Of these, it is preferable to use a styrene-butadiene-styrene block copolymer for its excellent thermal stability. In addition, as the tackifier and plasticizer, those that are in the state of being a solid under normal temperature can be used preferably, and as the tackifier, for example, C5-based petroleum resins, C9-based petroleum resins, dicyclopentadiene-based petroleum resins, rosin-based petroleum resins, polyterpene resins, terpene phenol resins, etc. can be listed and as the plasticizer, for example, besides monomeric plasticizers of tricresyl phosphate, dibutyl phthalate, and dioctyl phthalate, etc., polymeric plasticizers such as vinyl polymer and polyester can be listed.

Figure 4:
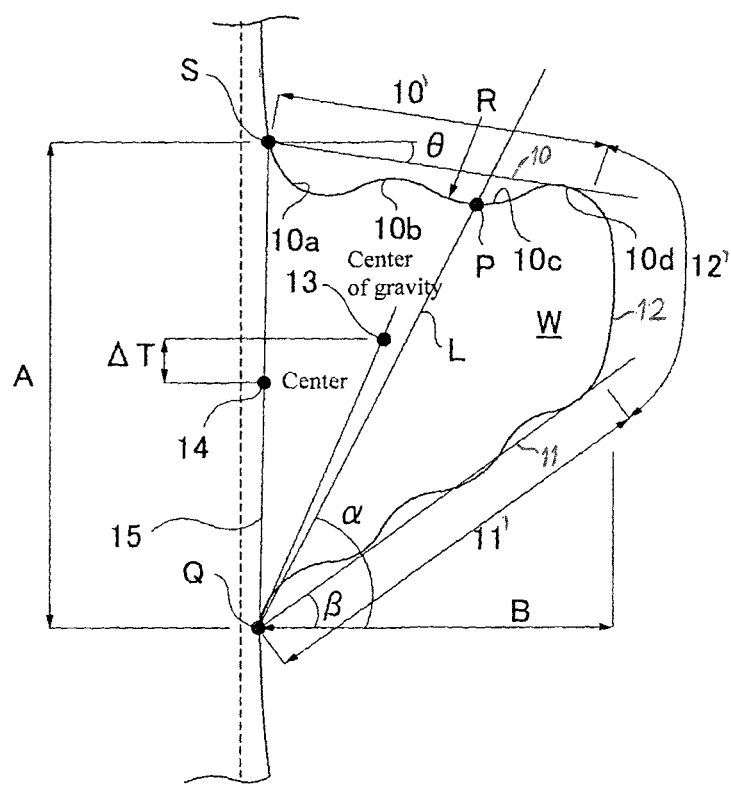
FIG. 4 is an enlarged plan view of the main section of a wing-shaped flap.

The wing-shaped flap (W), as illustrated in detail in FIG. 4, is of an outer shape formed of front profile line (10) that extends outwards from the main body section, rear profile line (11) that extends outwards from the main body section, and side profile line (12) that connects the front profile line (10) and rear profile line (11). (The lines (10'), (11') and (12') with arrows and approximately orthogonal lines at each end merely denote the extent of profile lines 10, 11 and 12, respectively,)

The front profile line (10) is a wave-shaped line formed by a repetition of convex portions that protrude outwards and concave portions that protrude inwards. The wave-shaped front profile line (10) is configured of, in order in the outwards direction beginning at its point of origin (S) at the base of the wing-shaped flap, first concave portion (10a), first convex portion (10b), second concave portion (10c), and second convex portion (10d). The second concave portion (10c) is what is referred to in the present invention as the "concave portion positioned in the most outwards position". Furthermore, an angle (α) formed by straight line (L) connecting vertex (P) of the concave portion (10c) positioned in the most outwards position and point of origin (Q) of the rear profile line of the wing-shaped flap (W) at the base of the wing-shaped flap (W) and a line also originating at point (Q) and extending outwardly orthogonally to a lengthwise axis of the sanitary napkin (1) is 60-65°. The radius of curvature (R) of the concave portion (10c) positioned in the most outwards position is preferably greater than or equal to 10 mm yet less than or equal to 20 mm and in order to keep the wave-shaped line balanced, it is preferable that the radius of curvature of the other first concave portion (10a), first convex portion (10b), and second convex portion (10d) is also greater than or equal to 10 mm yet less than or equal to 20 mm.

Although in the illustrated example the rear profile line (11) is a wave-shaped line formed by a repetition of convex portions that protrude outwards and concave portions that protrude inwards similar to the front profile line (10) the rear profile line may be a straight instead.

Concave portion (10c) positioned in the most outwards position is the position where the index finger of a hand catches on when the palm of the hand is placed to fold back wing-shaped flap (W). In other words, when angle (α) is 60-65°, when the user folds back wing-shaped flap (W), the index finger becomes precisely positioned at and catches on the concave portion (10c) such that shifting to the side is prevented, which makes it easier for the user to properly fold back wing-shaped flap (W) along the side edge of panties at the correct folding position (namely, along the base of the wing-shaped flap (W)).

Figure 6A:
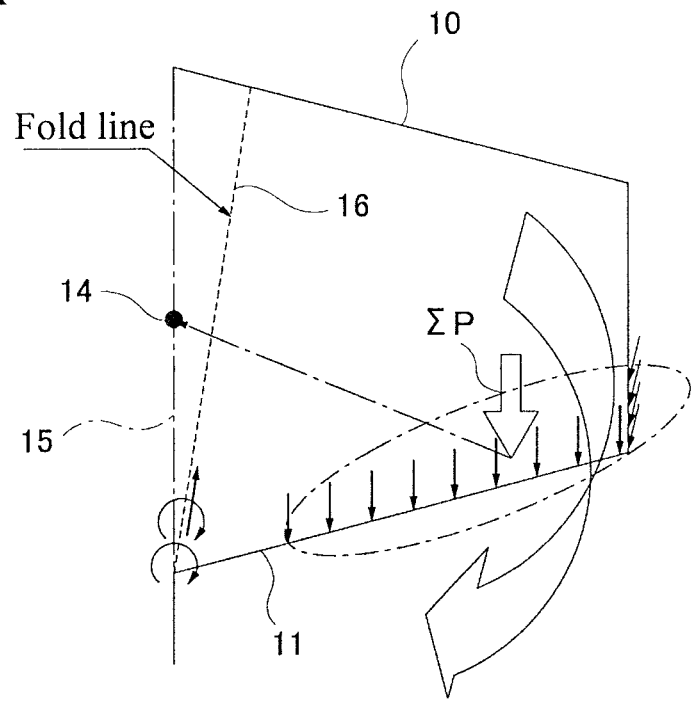
FIGS. 6A, 6B illustrate the mechanism of active threes when a wing-shaped flap is folded back where
Figure 6B:
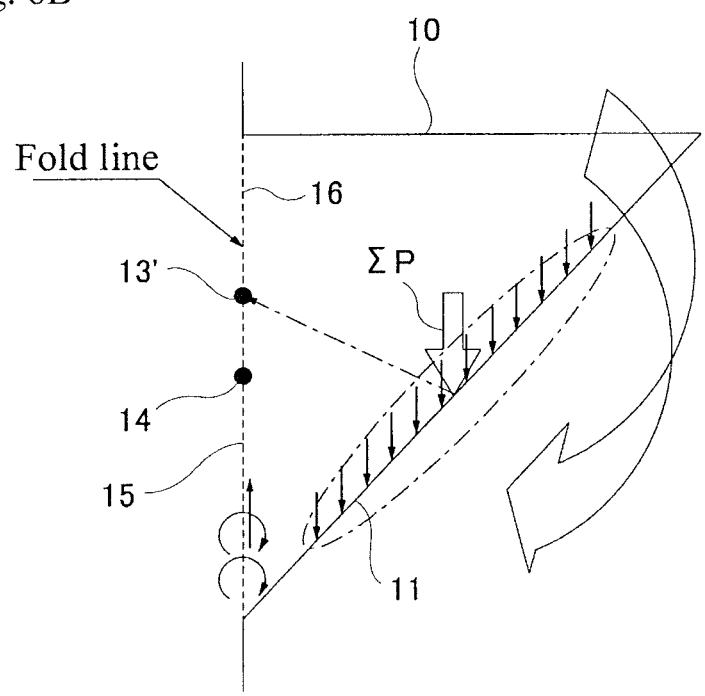

The shape of the wing-shaped flap (W) is configured such that angle (β) formed by a line originating at point (Q) and extending outwardly along the wing-shaped flap (W) orthogonally to a lengthwise axis of the sanitary napkin (1) and the rear profile line (11) is greater than angle (θ) formed by a line originating at point (S) and extending outwardly in a plane of the wing-shaped flap and orthogonally to a lengthwise axis of the sanitary napkin (1) and another line (10) originating at point (S) and tangential to the most outward convex portion (10d) of the wing-shaped flap (W). The center of gravity (13) of the wing-shaped flap is offset from the center point (14) of connecting line (15) where the base of wing-shaped flap (W) is connected to the main body section, the offset being a distance (ΔT) toward the front of the sanitary napkin (1) in the lengthwise direction thereof. Furthermore, to schematically illustrate shapes that satisfy the above-mentioned conditions, these may be an approximate triangle shape as illustrated in FIG. 6(A) or an approximate non-isosceles trapezoid shape as illustrated in FIG. 6(B). When this shape is an approximate triangle shape, side profile line (12) that connects front profile line (10) and rear profile line (11) will not exist.

Furthermore, the straight front profile line (10) in FIGS. 6(A) and 6(B) used to determine the angle (θ) corresponds to the line (10) in FIG. 4, and the rear profile line (11) in FIGS. 6(A), 6(B), 7(A) and 7(B) corresponds to the rear profile line in FIG. 4.

Figure 7A:
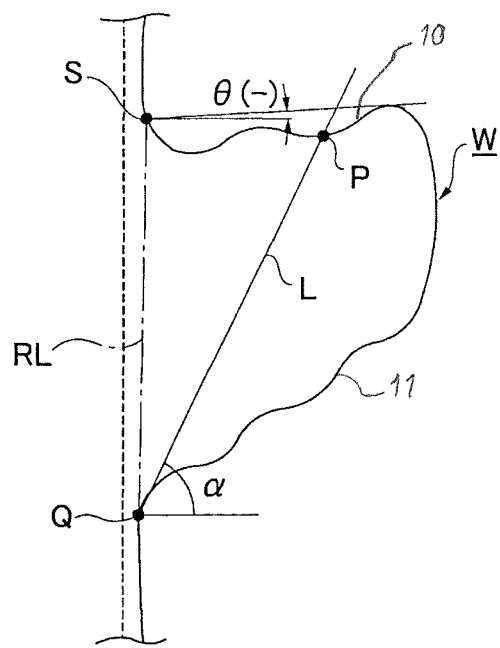
FIGS. 7A, 7B are schematic views illustrating other planar shapes of a wing-shaped flap according to the present invention.
Figure 7B:
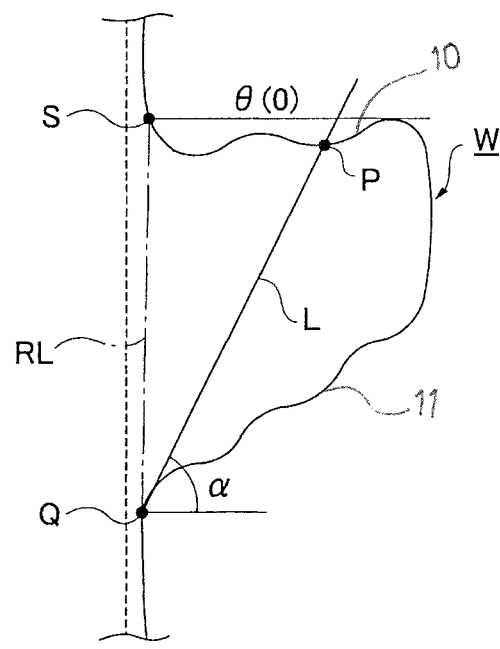

In regard to the front profile line (10), as illustrated in FIG. 7(A), it is possible for angle (θ) to be in a negative range where the front profile line (10) is a sloping line that slants towards the front of napkin (1) while extending outwards (instead of being in a positive range as in FIG. 4 where the front profile line is a sloping line that slants toward the rear of the napkin (1) while extending outwards), or, as illustrated in FIG. 7(B), it is possible for the angle (θ) to be 0 where the front profile line (10) is a horizontal line (i.e., orthogonal to a lengthwise axis of the sanitary napkin (1)). In the case that the angle (θ) formed with the front side profile line (10) is 0 or in a negative range, while it is possible to offset the center of gravity towards the front, it also makes it easier to fold back wing-shaped flap (W) as the hand can be placed on wing-shaped flap (W) across a greater area.

It is preferable that angle (θ) is approximately −10 to 15° and angle (β) is approximately 35 to 40°, in such case, it is preferable that the difference between angle (θ) and angle (β) is greater than or equal to 25°. When this difference of angles is greater than or equal to 25°, it is possible to ensure a sufficient distance (ΔT) and when folding back wing-shaped flap (W), as will be described later, even if the wing-shaped flap is folded back with a hand while the hand is moved towards the front, it becomes possible for the wing-shaped flap to be properly attached to panties in its correct state.

Figure 10:
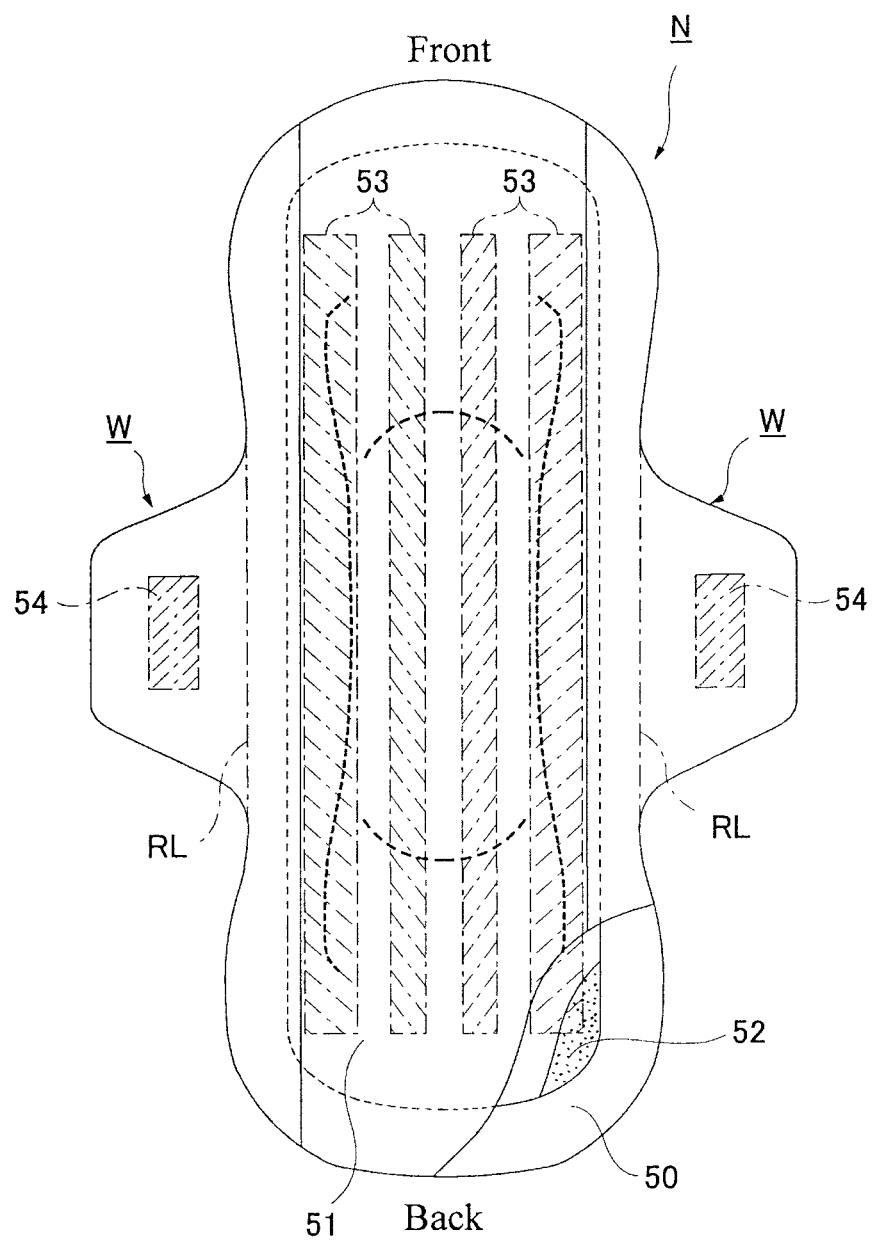
FIG. 10 is a development view of conventional napkin (N).
Figure 11:
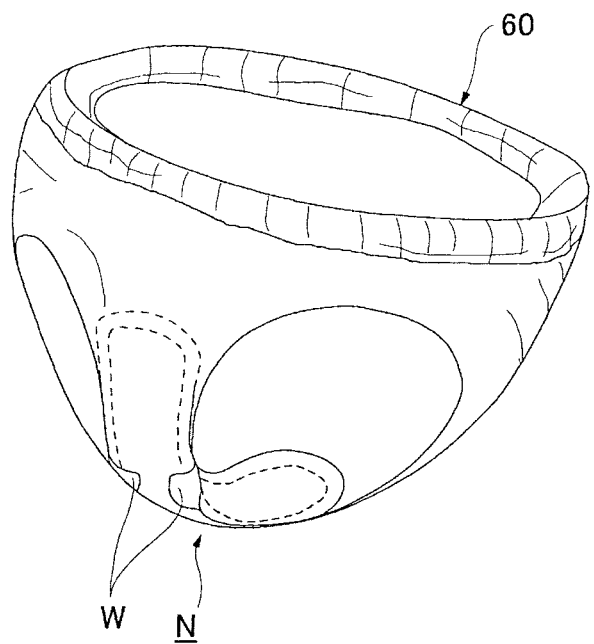
FIG. 11 is a diagram illustrating the state where conventional napkin (N) is attached.

By configuring wing-shaped flap (W) to be in the above-mentioned outer shape, it becomes possible to realize the advantage of enabling the wing-shaped flaps to be properly and easily folded back at their correct folding positions and attached without causing problems such as adhesives adhering to each other and incorrect adhesion, etc. This aspect will he further explained in detail with a comparison against a conventional isosceles trapezoid shaped wing shaped flap (W) (refer to FIG. 10).

First, when a woman attaches sanitary napkin (1) onto panties (20) while being seated on a toilet, etc., as this is done in a state where panties (20) are lowered, as illustrated in FIG. 5, the task of attaching napkin (1) is performed in front of the woman's body.

Figure 5A:
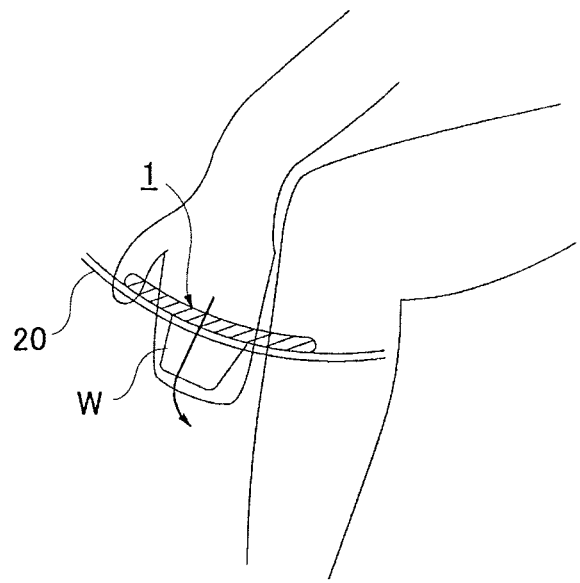
FIGS. 5A, 5B illustrate how a napkin is attached where
Figure 5B:
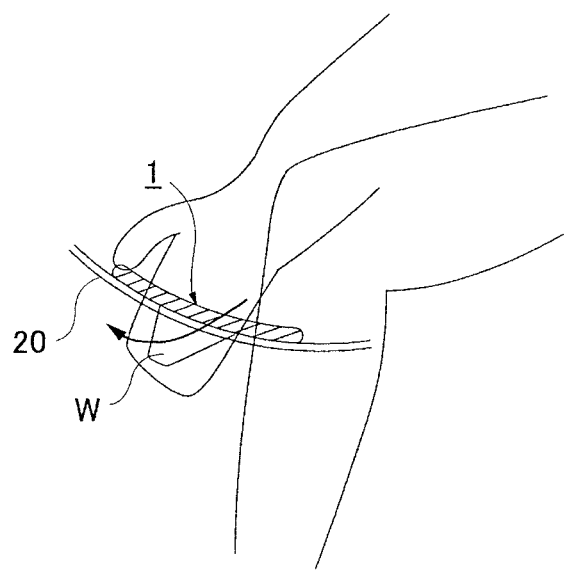

In the case of a conventional isosceles trapezoid-shaped wing-shaped flap (W), as illustrated in FIG. 5(A), the configuration is such that from a state where the hand is placed on both sides of the napkin, unless the wing-shaped flap is folded back straight downwards, the napkin cannot be properly attached. However, due to the position of attachment being on the front side of the body, unless care is taken, the hand is likely to include a forward moving motion (FIG. 5(B)) which could cause incorrect adhesion where only a single part of the wing-shaped flap is folded back and the adhesives adhere to each other to create wrinkles or a ridged area or where wing-shaped flap (W) is folded back halfway and the adhesives adhere to each other. In addition, there would also be cases where of the wing-shaped flap is folded back diagonally bent with respect to the intended fold line. In contrast to the above, when the wing shape is configured such that center of gravity (13) of the wing-shaped flap (W) is offset to the front side as in the present invention, as illustrated in FIG. 5(B), when folding back wing-shaped flap (W), it is possible to properly attach the flap in its correct state even if the wing-shaped flap is folded back with the hand while the hand is moved towards the front of the sanitary napkin (1).

While FIG. 6(A) illustrates the mechanism of active forces when a conventional isosceles trapezoid-shaped wing-shaped flap (W) is folded back, in the case that the wing-shaped flap is folded back with a hand while the hand is moved towards the front of the, based on how a force that acts in the downwards direction from the rear profile line of wing-shaped flap (W) is applied across the front profile, assuming that concentrated load (ΣP) summarizes the distributed loads thereof, the base point of the moment that is generated by this concentrated load (ΣP) becomes center point (14) of connecting line (15) of the wing-shaped flap, creating a twist when wing-shaped flap (W) is folded back and thus causing fold line (16) that gradually progresses from the base end of rear profile line (11) to tilt in the outwards direction.

In contrast to the above, in the case of the present invention, as illustrated in FIG. 6(B), based on how a downwards force acts on the center section of the slanted rear profile line (11) and assuming that concentrated load (ΣP) summarizes the distributed loads thereof, the base point of the moment that is generated by this concentrated load (ΣP) becomes center of gravity dividing point (13') (i.e., point 13', which is closer to the front of the sanitary napkin by a distance ΔT (see FIG. 4), divides the connecting line 15 into a segment extending to the base of the rear profile line 10 and a segment extending to the base of the front profile line, the ratio of the former to the latter in the embodiment of FIG. 6(B) being 1:2), and as there is very little twist when wing-shaped flap (W) is folded back, fold line (16) that gradually progresses from the base end of rear profile line (11) matches connecting line (15) thus enabling the flap to be folded back at its correct folding position.

In addition, as rear profile line (11) of wing-shaped flap (W) is of a greatly sloped shape, wing-shaped flap (W) can be properly folded at fold line (RL) without causing problems such as adhesives adhering to each other and incorrect adhesion, etc.

It is desirable that the distance between front origin (S) of the wing-shaped flap and side origin (Q) of the wing-shaped flap (dimension (A) of FIG. 4), namely the base end width of the wing-shaped flap, is configured to be less than or equal to 80 mm to fit within the curved portion of the crotch of panties, in addition, it is desirable that protruding length (B) (i.e., dimension orthogonal to length of the sanitary napkin) of the wing-shaped flap (W) is configured to be greater than or equal to 40 mm to make it easier for wing-shaped flap (W) to be pressed on by the palm of a hand when being folded back.

Figure 8:
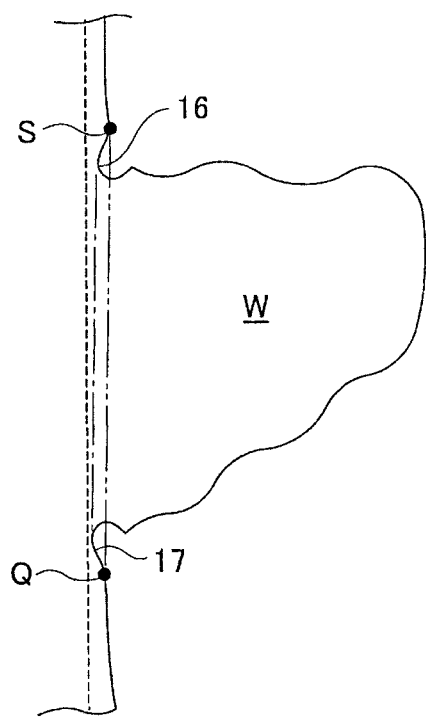
FIG. 8 is an enlarged plan view of a wing-shaped flap illustrating another example of a wing-shaped flap according to the present invention.

Other embodiments are described hereinbelow with reference to FIGS. 8 and 9. As illustrated in FIG. 8, it is possible to have cutout portions (16, 17) that dip into the main body section of napkin (1) at connecting portion (S) where front profile line (10) of the wing-shaped flap (W) connects to the main body section of napkin (1) and at connecting portion (Q) where rear profile line (11) of the wing-shaped flap connects to the main body section of napkin (1). As such configuration causes wing-shaped flap (W) to be folded back within the cutout portions (16, 17) when being folded back, this facilitates the wing-shaped flap (W) to be properly folded back at its correct folding position (base position).

Figure 9:
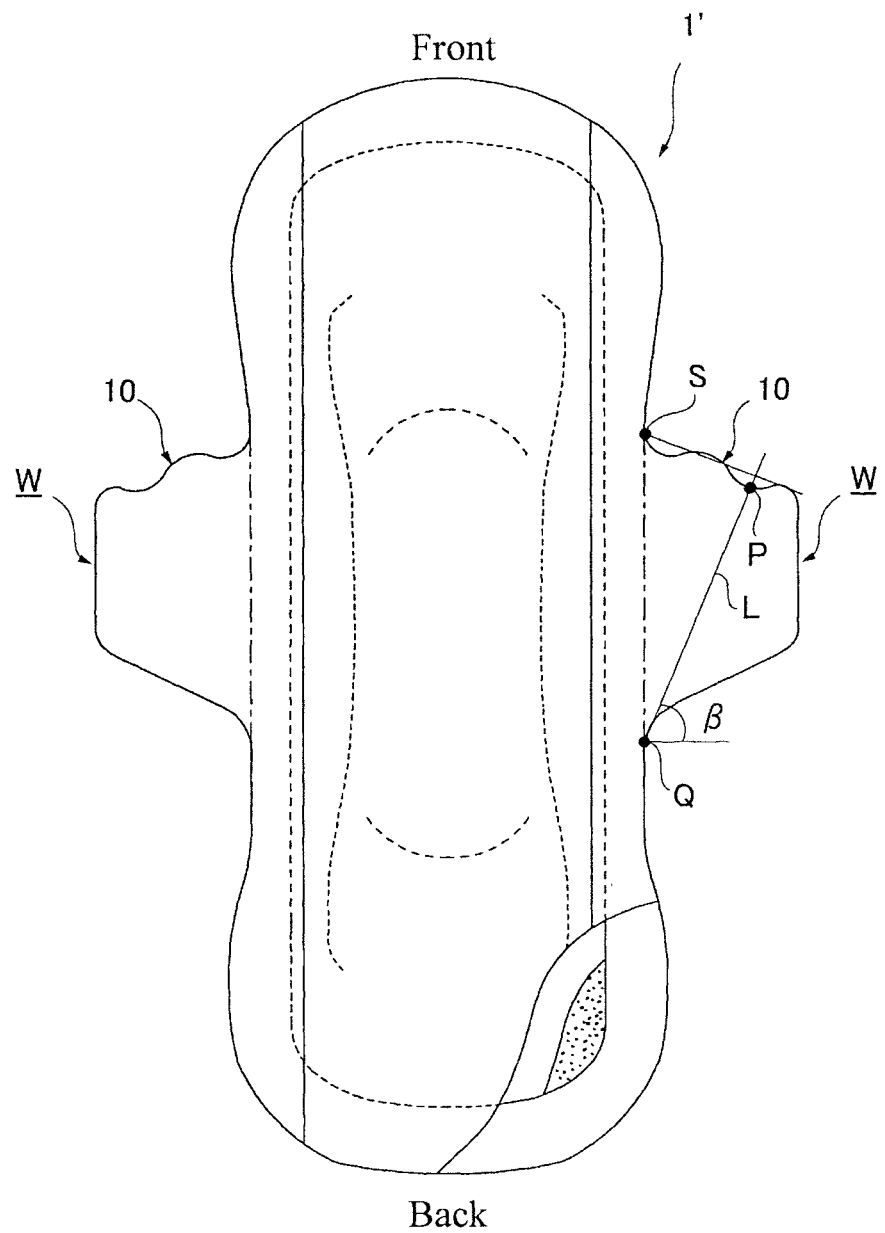
FIG. 9 is a plan view of a napkin illustrating another embodiment of the present invention.

Although in the aforementioned embodiments, wing-shaped flap (W) is configured such that angle (β) is greater than angle (θ) and center of gravity (13) of the wing shaped flap (W) is offset by (ΔT) to be on the front side of center point (14) of connecting line (15) where the base of wing-shaped flap (W) is connected to the main body section, as illustrated in FIG. 9 it is possible to apply the present invention to a conventional isosceles trapezoid-shaped wing-shaped flap (W), configure front side profile line (10) thereof to he a wave-shaped line formed by a repetition of convex portions that protrude outwards and concave portions that protrude inwards, and configure straight line (L) connecting vertex (P) of concave portion (10c) positioned in the most outwards position and rear side origin (Q) of the wing-shaped flap (W) to be at an angle (α) of 60-65° in relation to a line orthogonal to the length of napkin (1) and passing through the rear side origin (Q).

By configuring the wing-shaped flap (W) of a material having elasticity in the longitudinal direction and/or lateral direction of the napkin, wing-shaped flap (W) will follow the movement of the body and alleviate stress, the sanitary napkin is more comfortable and less susceptible to displacement when worn. More specifically, by using a side non-woven fabric having elasticity, or yet more specifically a non-woven fabric configured of long fibers formed of an elastic resin material such as polyurethane that is easily plastically deformed in a reversible manner or a non-woven fabric provided with elasticity by having zigzag-shaped or coil-shaped crimps and allowing these crimps to be extended instead of the fiber diameter of each fiber itself changing upon being stretched, etc. as the side non-woven fabric (7) while also using an elastic plastic film as the liquid-impermeable backing sheet 2, the wing-shaped flaps (W, W) are provided with elasticity, thus enabling the flaps to follow movement of the body.

The invention claimed is:

1. An absorbent article to be worn around the crotch of a person, the absorbent article having front and rear ends to be positioned at the front and rear, respectively, of the person, the absorbent article extending lengthwise in a direction from the front to the rear of the absorbent article, the absorbent article comprising
   a main body having a lengthwise section at which an absorbent body is interposed between a liquid-permeable surface sheet and a liquid-impermeable backing sheet, and
   a respective wing-shaped flap extending laterally from each side of said main body section, each of the flaps to be wrapped around a crotch section of underwear for securing the absorbent article to the underwear, wherein
   each of said wing-shaped flaps have a front profile line that extends outwards from the main body section and a rear profile line that extends outwards from the main body section,
   said front profile line is a wave-shaped line formed by a repetition of convex portions that protrude outwards and concave portions that protrude inwards and
   an angle α formed by a straight line connecting a vertex of the concave portion positioned in a most outwards position and a first connecting point where the rear profile line of said wing-shaped flaps connects to the main body and a line also originating at the first connection point and extending outwardly orthogonally to the length of the absorbent article is 60-65°.

2. The absorbent article according to claim 1, wherein
   an angle β formed by the line originating at the first connection point where the rear profile line connects with the main body and extending orthogonally to the length of said absorbent article and said rear profile line is greater than the angle θ formed by a line originating at a second connection point where the front profile line of said wing-shaped flaps connects to the main body and extending orthogonally to the length of said absorbent article and said front profile line, and
   a center of gravity of said wing-shaped flap is forward, in the lengthwise direction of the absorbent article, of a point midway between the first and second connection points.

3. The absorbent article according to claim 2, wherein the distance between the first and second connecting points is less than or equal to 80 mm and each of said wing-shaped flaps extends outwardly from the main body by a distance greater than or equal to 40 mm.

4. The absorbent article according to claim 1, wherein the radius of curvature of said concave portion positioned in the most outwards position is greater than or equal to 10 mm and less than or equal to 20 mm.

5. The absorbent article according to claim 1, further comprising, adjacent each of the connection points, a cutout portion extending into the wing-shaped flap and the main body.

\* \* \* \* \*